United States Patent [19]

Kim

[11] Patent Number: 4,871,870

[45] Date of Patent: Oct. 3, 1989

[54] IMMUNOMODULATORS AND METHOD OF MAKING SAME

[75] Inventor: Sun H. Kim, Chestnut Hill, Mass.

[73] Assignee: Biomeasure, Inc., Hopkinton, Mass.

[21] Appl. No.: 25,850

[22] Filed: Mar. 16, 1987

[51] Int. Cl.$^4$ .......................................... C07C 101/30
[52] U.S. Cl. .................... 560/039; 562/448; 560/312; 549/426
[58] Field of Search ..................... 560/39, 40; 562/448

[56] References Cited

U.S. PATENT DOCUMENTS 4,552,866 11/1985 Delaney et al. ........................ 514/16

FOREIGN PATENT DOCUMENTS 444838 2/1968 Switzerland .

OTHER PUBLICATIONS

Nishizawa et al., J. of Antibiotics, 36:695 (6/83).
European Patent Application, No. 2,037,754 (7/16/80).
Nahm et al., Tetrahedron Letters, 22:3815 (1981).
Rich et al., Abstract, "Mechanism of Inhibition of Aminopeptidases by Bestatin and Related Analogs".

Primary Examiner—Paul J. Killos
Attorney, Agent, or Firm—Fish & Richardson

[57] ABSTRACT

A compound having the formula

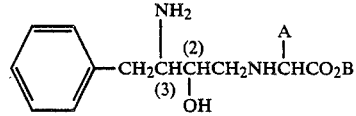

or a pharmaceutically acceptable salt thereof, wherein A is an amino acid identifying group; B is a hydrogen atom, an alkyl group having 1-5, inclusive, carbon atoms, or an aralkyl group having 6-12, inclusive, carbon atoms; carbon atom 2 is of the R configuration; and carbon atom 3 is of the R configuration. The compounds of the invention are effective in augmenting immunological responses and are useful therefore in the treatment of diseases such as cancer, viral infections, bacterial infections, and arthritis.

4 Claims, No Drawings

IMMUNOMODULATORS AND METHOD OF MAKING SAME

BACKGROUND OF THE INVENTION

This invention relates to immunomodulators.

Nonspecific immunotherapy usually involves the use of immunomodulating agents administered with the aim of either general stimulation of or general suppression of a person's immune system. General immunostimulation enhances the ability of the immune system to respond to various diseases, e.g., cancer, bacterial infections, and virus infections, and thus can be a useful treatment for these disorders.

One example of an immunostimulating agent is bestatin (N-[(2S, 3R)-3-amino-2-hydroxy-4-phenylbutyl]-L-leucine), an amino acid derivative isolated from culture filtrates of Streptomyces olivoreticuli. A synthesis of bestatin is described in Nighizawa et al., 36 J. Antibiotics 695, and in British Pat. No. 2,037,754.

SUMMARY OF THE INVENTION

The invention features, in one aspect, a compound having the formula:

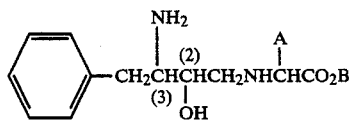

or a pharmaceutically acceptable salt thereof, wherein A is an amino acid identifying group; B is a hydrogen atom, an alkyl group having 1-5, inclusive, carbon atoms, or an aralkyl group having 6-12, inclusive carbon atoms; carbon atom 2 is of the R configuration; and carbon atom 3 is of the R configuration.

The term amino acid identifying group, as used herein, refers to the Z portion in the following amino acid structure:

The Z portions of the common amino acids can be found in Lehninger, Biochemistry 73-75 (2d ed. 1975).

The invention features, in another aspect, a compound having the formula

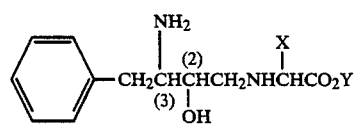

or a pharmaceutically acceptable salt thereof, wherein X is H or an alkyl group having 1-6 carbon atoms, inclusive, carbon atoms; Y is a hydrogen atom, an alkyl group having 1-5, inclusive, carbon atoms, or an aralkyl group having 6-12, inclusive, carbon atoms; carbon atom 2 is of the R configuration; and carbon atom 3 is of the R configuration.

In preferred embodiments, Y is a hydrogen atom. Preferred compounds include N-[(2R, 3R)-3-amino-2-hydroxy-4-phenylbutyl]-L-leucine and N-[(2R, 3R)-3-amino-2-hydroxy-4-phenylbutyl]-L-isoleucine.

The invention features, in another aspect, a method of synthesizing a first compound having the formula

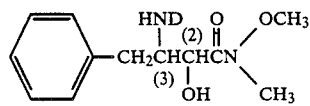

wherein D is an acyl group having between 1-6, inclusive, carbon atoms or an arylacyl group (e.g., benzoyl and benzyloxycarbonyl) having between 7-12, inclusive, carbon atoms, the method comprising the steps of: (1) providing a second compound having the formula

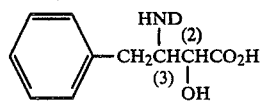

wherein D is as defined above; and (2) condensing said second compound with N,O-dimethylhydroxylamine hydrochloride, or a salt thereof, to form the first compound.

In preferred embodiments, the condensing step is carried out in the presence of a dehydrating agent such as dicyclohexylcarbodiimide, and in the presence of 1-hydroxybenzotriazole.

The compounds of the invention are effective in augmenting immunological responses and are useful therefore in the treatment of diseases such as cancer, viral infections, bacterial infections, and arthritis. The compounds are stable and non-toxic.

Other features and advantages of the invention will be apparent from the following description of the preferred embodiments, and from the claims.

DESCRIPTION OF THE PREFERRED EMBODIMENTS

We now describe the structure, synthesis, and use of the preferred embodiments.

STRUCTURE

The compounds of the invention have the general formulae recited in the summary of the invention above. Examples of preferred compounds within these formulae are those referred to as preferred embodiments above.

The compounds of the invention are 3-amino-2-hydroxy-4-phenylbutane derivatives in which the carbon atom 1 is bonded to the α-amino group of an amino acid; carbon atom 2 and carbon atom 3 of the butyl portion of the compounds are of the R configuration.

The compounds can also be provided in the form of pharmaceutically acceptable salts. Examples of suitable salts include those formed with hydrochloric, hydrobromic, sulfuric, maleic, acetic, ascorbic, succinic, citric, or fumaric acid; potassium, sodium, or aluminum hydroxide; or dicyclohexylamine.

SYNTHESIS

The above compounds can be synthesized as follows.

First, a compound of formula (1), where D is as defined above, carbon atom 2 is of the S configuration, and carbon atom 3 is of the R configuration, is condensed with

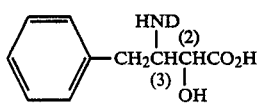 (1)

N,O-dimethylhydroxylamine hydrochloride in the presence of a dehydrating agent such as dicyclohexyl-carbodiimide to give a derivative having formula (2). Most preferably, the condensation is carried out in the presence of 1-hydroxybenzotriazole hydrate, which helps keep racemization to a minimum.

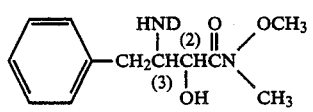 (2)

The 2-hydroxy group of compound (2) is then protected with a blocking group that is resistant to reduction by lithium aluminum hydride (e.g., a tetrahydropyranyl, methoxymethyl (MOM), or 2-methoxyethoxymethyl (MEM)) to give a compound having formula (3) (which shows the 2-hydroxy blocked with a tetrahydropyranyl group).

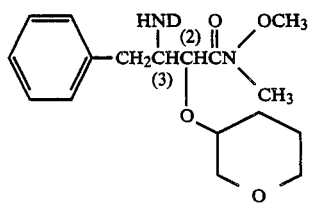 (3)

The N,O-dimethylhydroxamate group of compound (3) is then reduced to an aldehyde having formula (4) by reaction with lithium aluminum hydride (see J. March, Advanced Org. Chem. 398 (3d ed. 1985), and the references cited therein; Tet. Lett. 22 3815 (1981)), followed by treatment with aqueous sodium sulfate.

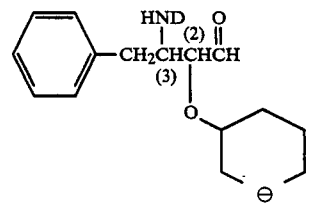 (4)

The aldehyde of compound (4) is then condensed with an α-amino group of an amino acid ester of formula (5), where E is either A or X as defined above and F is hydrogen or an alkyl group having 1–5, inclusive, carbon atoms, or an aralalkyl group

 (5)

H$_2$NCHCO$_2$F having 6–12, inclusive, carbon atoms, to give a compound of formula (6).

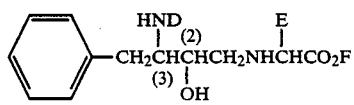 (6)

The condensation can be carried out, for example, in the presence of sodium cyanoborohydride and triethylamine, or by catalytic hydrogenation, e.g., in the presence of palladium on carbon or Rainey nickel (see March, supra, at 798).

The ester, amide, and tetrahydropyranyl linkages are then hydrolyzed in the presence of acid to give the final product (formula (7)).

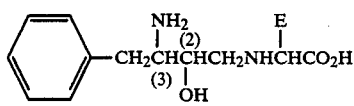 (7)

The ester of a compound of formula (6) can be prepared by reacting that compound with an appropriate alcohol in the presence of a catalytic amount of acid.

The intermediate and final products are isolated and purified by standard methods, e.g., column chromatography or crystallization. Purity is determined using chromatographic, spectroscopic, and chemical analysis.

A compound of the invention, N-[(2R, 3R)-3-amino-2-hydroxy-4-phenylbutyl]-L-leucine hydrochloride, was made as follows (compounds a–d are intermediates in the synthesis).

a.

(2S,3R)-3-Acetamido-2-hydroxy-4-pheynylbutanoic acid N,O-dimethylhydroxamate

A solution of (2S,3R)-3-acetamido-2-hydroxy-4-phenylbutanoic acid (3.56 g, 15 mmoles), synthesized by the method described by Umezawa et al., J. Antibiotics 34 695, and N,O-dimethylhydroxylamine hydrochloride (1.16 g, 16.5 mmoles) in 100 ml dichloromethane and 20 ml dimethylformamide was cooled in an ice bath under dry conditions. N-Methylmorpholine (2.2 ml, 19.5 mmoles) was added and the mixture stirred 5 minutes. 1-Hydroxybenzotriazole hydrate (4.1 g, 30 mmoles) was added, followed by an ice-cold solution of 4.0 g dicyclohexylcarbo-diimide (19.5 mmoles) in 10 ml dichloromethane. The reaction mixture was stirred in the ice-bath for two hours, then overnight at room temperature.

The white solid (dicyclohexylurea) formed was then filtered out from the reaction mixture. Dichloromethane was added to the filtrate, which was washed 3 times with H$_2$O, then 3 times with 5% NaHCO$_3$. The organic phase was dried over anh. MgSO$_4$, filtered, and the solvent removed in vacuo to yield 4.04 g of a yellow viscous residue.

The product can be isolated from the crude residue by either silica gel chromatography (using a mobile phase of 30:1 chloroform/methanol) or by recrystallization from ethyl acetate/hexane. The yield when the former is used was 2.3 g of white solid (55%). TLC (silica gel: CHCl$_3$/MeOH 9/1) Rf=0.50.

b.

(2S,3R)-3-Acetamido-2-tetrahydropyranyloxy-4-phenylbutanoic acid N,O-dimethylhydroxamate To a solution of (2S,3R)-3-acetamido-2-hydroxy-4-phenylbutanoic acid N,O-dimethylhydroxamate (0.7 g, 2.5 mmoles) and dihydropyran (0.6 g, 7.5 mmoles) in 15 ml dry tetrahydrofuran was added 0.02 g p-toluenesulfonic acid (0.1 mmole, catalytic amount). The sealed reaction flask was stirred at room temperature overnight.

5 ml of 5% aq. NaHCO$_3$ was then added to the reaction mixture, and the organic solvent was removed in vacuo. 5 ml H$_2$O was added and the mixture extracted 3 times with chloroform. The combined chloroform extracts were dried over anh. MgSO$_4$, and the solvent removed to yield 1.1 g of a viscous oil.

The product was further purified by chromatography on alumina oxide 90-neutral (stage III) using 1:2 hexane/ethyl acetate mobile phase. Purification yielded 0.81 g of a clear oil which solidified upon standing to a white solid (90% yield). TLC (silica gel: CHCl$_3$/MeOH 20/1, Rf=0.60) or (alumina oxide: Hexane/EtOAc 1/2, Rf=0.35).

c.

(2S,3R)-3-Acetamido-2-tetrahydropyranyloxy-4-phenylbutyraldehyde

A solution of (2S,3R)-3-acetamido-2-tetrahydropyranyloxy-4-phenylbutanoic acid N,O-dimethylhydroxamate (2.03 g, 5.6 mmoles) in 30 ml anhydrous THF was cooled in an ice-bath in a 3-neck flask kept under nitrogen. Portionwise addition of lithium aluminum hydride (0.27 g, 7 mmoles) was made over a 45 minute period. Stirring was continued under nitrogen at 0°; after 5 hours, 60 ml of saturated aq. Na$_2$SO$_4$ was slowly added, and stirring continued for 30 minutes.

The stirring was stopped, allowing some of the aluminum salt solids to settle. The supernatant was decanted and the residue washed gently wwith sat. Na$_2$SO$_4$, which was added to the initial supernatant. The aqueous phase was extracted 4 times with ethyl acetate. The combined organic extracts were dried over anh. MgSO$_4$, filtered, and the solvent removed in vacuo to yield 1.9 g of clear viscous oil. The crude product was used directly in the next reaction. TLC (alumina oxide: Hexane/EtOAc 1/2) Rf=0.25.

d.

N-[(2R,3R)-3-Acetamido-2-tetrahydropyranyloxy-4-phenylbutyl]-L-leucine methylester To a solution of L-leucine methylester hydrochloride (1.09 g, 6.0 mmoles) in 11 ml methanol was added triethylamine (0.4 ml, 3.0 mmoles). The reaction mixture was stirred for 5 minutes, at which time the pH was about 7. The crude aldehyde residue (1.9 g) dissolved in 20 ml methanol was added. Over a 60 minute period, sodium cyanoborohydride (0.76 g, 12 mmoles) was added portionwise. The reaction flask was sealed, and stirring was continued overnight at room temperature.

Sixty ml of 5% aq. NaHCO$_3$ was then added to the reaction mixture with stirring. The mixture was extracted with ethyl acetate 4 times, the organic extract was dried over anh. MgSO$_4$, and the solvent removed in vacuo to obtain 2.6 g of a viscous residue.

The product was purified from the crude residue by silica gel chromatography using 30:1 a chloroform/methanol at the mobile phase to yield 0.95 g of product. TLC (silica gel: CHCl$_3$/MeOH 9/1) Rf=0.5.

N-[(2R,3R)-3-Amino-2-hydroxy-4-phenylbutyl]-L-leucine hydrochloride

A solution of N-[(2R,3R)-3-acetamido-2-tetrahydropyranyloxy-4-phenylbutyl]-L-leucine methylester (1.0 mmole) was refluxed in a solution of acetone (2 ml) and 6N HCL (8 ml) overnight. The solvent was evaporated to obtain an off-white solid (0.39 g), which was then purified by silica gel chromatography using 5:1:0.1 chloroform:methanol:acetic acid. TLC (silica gel: CHCl$_3$/MeOH/HOAc 3/1/0.1) Rf=0.20.

USE

When administered to a patient (e.g., orally, intraveneously, parenterally, nasally, or by suppository), the compounds stimulate the immune system and thus are effective in the treatment of, for example, cancer, viral infections, bacterial infections, and arthritis.

The compounds can be administered to a human patient in a daily oral dosage of about 1–100 mg/kg/day, more preferably 30–60 mg/kg/day.

A therapeutic composition containing the compounds of the invention should contain no more than 20% (more preferably no more than 10%; most preferably no more than 2%) by weight of the 2R,3S; 2S,3R; and 2S,3S stereoisomers.

OTHER EMBODIMENTS

Other embodiments are within the following claims. For example, the compound N-[(2R,3R)-3-amino-2-hydroxy-4-phenylbutyl]-L-leucine hydrochloride (described above) can be prepared by an alternative method from (2S,3R)-3-acetamido-2-hydroxy-4-phenylbutanoic acid by, first, converting the 4-carboxylic acid to the methyl ester; second, reducing the 4-ester to the aldehyde using DiBal; third, performing a reductive amination of the aldehyde with L-leucine methyl ester using sodium cyanoborohydride or sodium borohydride; and finally, hydrolyzing the methyl ester and acetamide groups in the presence of acid.

The compound of formula (2) can also be made by the standard mixed anhydride method.

I claim:

1. A compound having the formula:

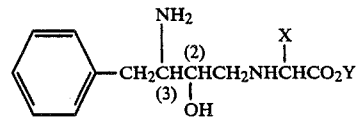

or a pharmaceutically acceptable salt thereof,
wherein X is H or an alkyl group having 1-6, inclusive, carbon atoms;
Y is a hydrogen atom, an alkyl group having 1-5, inclusive, carbon atoms, or an aralkyl group having 6-12, inclusive, carbon atoms;
carbon atom 2 is of the R configuration; and
carbon atom 3 is of the R configuration.

2. The compound of claim 1, wherein Y is a hydrogen atom.

3. The compound having the name N-[(2R,3R)-3-amino-2-hydroxy-4-phenybutyl]-L-leucine.

4. The compound having the name N-[(2R,3R)-3-amino-2-hydroxy-4-phenylbutyl]-L-isoleucine.

* * * * *

UNITED STATES PATENT AND TRADEMARK OFFICE
CERTIFICATE OF CORRECTION

PATENT NO. : 4,871,870
DATED : October 3, 1989
INVENTOR(S) : Sun H. Kim

Page 1 of 2

It is certified that error appears in the above-identified patent and that said Letters Patent is hereby corrected as shown below:

Column 3, line 55, "θ" should be replaced with --O--;

Column 4, line 37, correct the spelling of "phenylbutanoic";

Column 4, line 50, correct the spelling of "dicyclohexylcarbodiimide";

Column 5, line 41, correct the spelling of "with";

Column 6, claim 3, line 65, correct the spelling of "phenylbutyl".

UNITED STATES PATENT AND TRADEMARK OFFICE
CERTIFICATE OF CORRECTION

PATENT NO. : 4,871,870
DATED : October 3, 1989
INVENTOR(S) : Sun H. Kim

It is certified that error appears in the above-identified patent and that said Letters Patent is hereby corrected as shown below:

Col. 1, line 17, "phenylbutyl" should be replaced with --phenylbutanoyl--;

Col. 6, claim 1, lines 58-59, change "having 6-12" to --having up to 12--.

Signed and Sealed this

Twenty-eighth Day of August, 1990

Attest:

HARRY F. MANBECK, JR.

Attesting Officer     Commissioner of Patents and Trademarks